United States Patent [19]

Schmidt

[11] 4,448,074
[45] May 15, 1984

[54] SOFT-SWITCHING AUDIOMETER

[75] Inventor: Wolfgang Schmidt, Berlin, Fed. Rep. of Germany

[73] Assignee: Robert Bosch GmbH, Stuttgart, Fed. Rep. of Germany

[21] Appl. No.: 345,224

[22] Filed: Feb. 3, 1982

[30] Foreign Application Priority Data

Mar. 6, 1981 [DE] Fed. Rep. of Germany ....... 3108407

[51] Int. Cl.³ ............................................. A61B 5/12
[52] U.S. Cl. ..................................... 73/585; 381/123; 381/94
[58] Field of Search .................... 179/1 N, 1 P, 1 SW; 73/585; 381/56, 94, 123

[56] References Cited

PUBLICATIONS

American National Standard Specifications for Audiometers, 6/19/1969, copyright 1970.

*Primary Examiner*—A. D. Pellinen
*Assistant Examiner*—James L. Dwyer
*Attorney, Agent, or Firm*—Frishauf, Holtz, Goodman & Woodward

[57] ABSTRACT

To provide both for soft-switching, that is, elimination of switching clicks, and rapid rise and decay of tone supply from a frequency generator (10) to an audio transducer (13), two electronic switches (11, 16) are provided, one interrupting connection from the source to an audio amplifier amplifying the signals for the transducer, and the other (16) effectively short-circuiting the amplifier, the switches having current transfer/time characteristics to provide for gradual current rise and current decay through the amplifier, and hence gradual rise and drop of the level of output from the transducer with sufficiently steep flanks, however, to effectively eliminate harmonics and hence high-frequency switching clicks. Typical switches use opto couplers with an instantaneous ON optical element such as a light emitting diode (30, 36) illuminating a photo resistor (31, 37) which has resistance change vs. time characteristics following an exponential function. Preferably, a third electronic switch, for example a field effect transistor (FET) is connected across the input of the amplifier. Timing circuits, which may provide for gradual current variation or delayed switching effects can be included serially between a control unit (24, 25, 26, R) and the controlled electronic switches.

14 Claims, 5 Drawing Figures

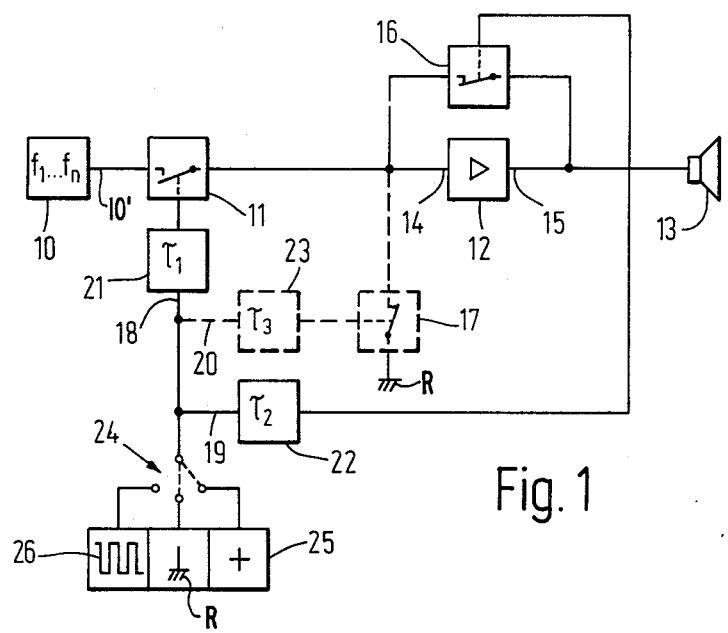
Fig. 1
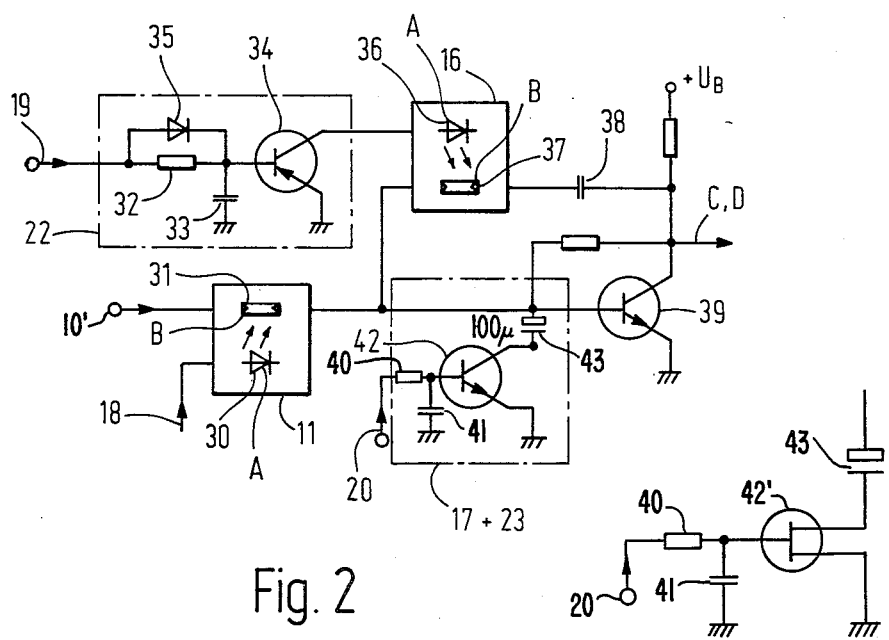
Fig. 2
Fig. 2a

SOFT-SWITCHING AUDIOMETER

The present invention relates to a medical test instrument, and more particularly to an audiometer which has soft switching characteristics.

BACKGROUND

Audiometers, particularly audiometers for use on small children or babies, where frequent frequency changes are used to retain the subject's attention, have the additional requirement that switching between frequencies, or between ON-OFF, must be soft, that is, must be such that switching clicks or thumps upon change in frequency, or volume of tone are avoided. Switching clicks are not only annoying to the test subject, but additionally interfere with proper testing. Such switching clicks usually are formed by a group of frequencies of an extended band of frequencies. The American National Standard Institute (ANSI) has developed a specific standard for audiometers which, among others, requires switching without clicks and free from higher harmonics. This condition, by and itself, can be met by raising the level of the tone signal comparatively slowly upon first connecting the tone signal and then, likewise, dropping the level slowly upon disconnection. This solution is not entirely satisfactory, however, since it is in conflict with a further standard of the ANSI which requires short switching times, that is, a relatively steep rise in level, and steep decay or drop in level, upon turn-off. The difference in level, that is, the suppression of sound when the sound is OFF, should be at least 60 dB.

The problem of suppression of switching clicks or thumps has particular significance if the tone signal is to be connected ON and OFF at a high rate so that, for example when testing babies, a high degree of attention is insured.

THE INVENTION

It is an object to provide an audiometer which meets both of the ANSI requirements—absence of switching clicks with rapid change in level—and which is simple and reliable while providing a high degree of suppression of tone when switched to OFF state.

Briefly, an amplifier, which is connected to a transducer, such as a loudspeaker, earphones, or the like, is connected in series with a first switch which, in turn, is connected to the audio tone generator. A second electronic switch is connected across the amplifier; in accordance with a feature of the invention, which is preferred, a third electronic switch may be connected to the input resistor of the amplifier, that is, when closed, to bridge the input resistor.

The two—or, if used, the three—switches have an ON-OFF switching timing characteristic, such that the frequencies connected from the frequency generator to the amplifier and through the amplifier to the transducer will have a rise and decay level—with respect to time—such that switching clicks are avoided while, however, still providing for substantially rapid rise and decay.

In accordance with a preferred feature of the invention, the electronic switches include opto couplers with light-sensitive resistors which have a finite time-resistance change characteristic upon being exposed to light. Thus, the opto couplers can be used for instantaneous energization of the light source with, however, some time delay of resistance change of the opto coupler resistance which is just enough to suppress switching clicks, but not long enough to interfere with rapid rise or decay in level of the tone being reproduced.

In accordance with a preferred feature of the invention, an additional timing circuit can be introduced to the switch to modify the level change vs. time characteristic to accurately match the performance of the audio meter to the standards or specifications required by the ANSI and other design conditions.

DRAWINGS

FIG. 1 is a simplified block diagram of the audiometer;

FIG. 2 is a circuit diagram of the essential components for click-free switching of the audiometer;

FIG. 2a is a fragmentary diagram showing a modification of the circuit of FIG. 2

Figure 3:
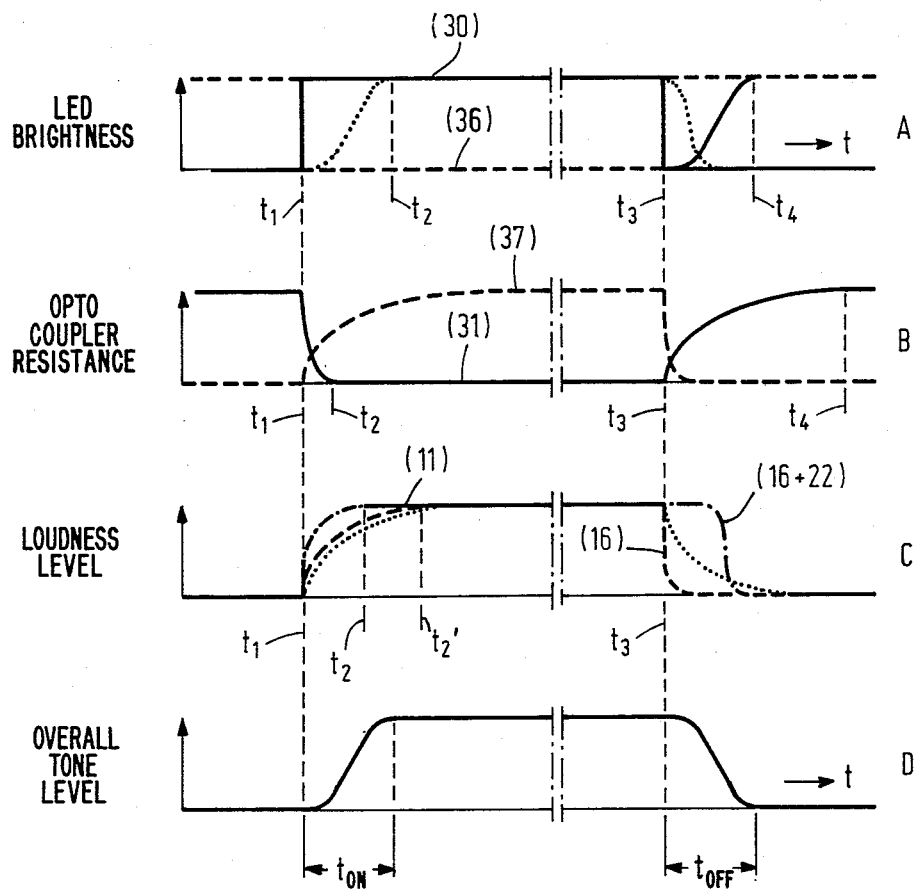
FIG. 3 is a series of superposed timing diagrams illustrating brightness, resistance, loudness, and overall loudness reproduction upon switching a tone signal ON and OFF.

The tone audiometer—see FIG. 1—has a frequency generator 10 which provides at its output one of a multiplicity of selectable frequencies $f_1 \ldots f_n$. The audio tone frequency generator 10 is connected through a first controlled electronic switch 11—preferably an opto coupler—to an audio amplifier 12. The audio amplifier 12 has a variable degree of amplification. Audio amplifier 12 has an input terminal 14 and an output terminal 15. Its output terminal is connected to a transducer 13, for example a loudspeaker, earphones to be worn by the subject to be tested, or the like.

A second controlled electronic switch 16 is connected across the input and output terminals 14, 15 of the amplifier 12. The switch 16, preferably, also is an opto coupler.

In accordance with a feature of the invention which, however, is not necessary and therefore not shown in solid lines, a third controlled electronic switch 17 can be provided which, when closed, connects the input 14 of the audio amplifier 12 to a reference voltage, for example ground or chassis.

Each one of the electronic switches 11, 16, 17 are connected to a respective control line 18, 19, 20 in which, each, a timing circuit 21, 22, 23, respectively, is connected. The timing circuit 23 preferably is a dead-time element which passes a switching pulse from line 20 to the associated switch 17 only after a predetermined time interval has elapsed.

The control lines 18, 19, 20 which carry the control signals for the switches 11, 16 and 17, if used, are connected to a switch control unit which includes a transfer switch 24 which is in turn connected, selectively, to (a) a control voltage source 25;
(b) ground, or reference R; or
(c) a pulse source supplying pulses 26.

Depending on the selected position of switch 24, the lines 18, 19, 20 will have applied thereto (a) a predetermined positive voltage;
(b) ground, or reference voltage R; or
(c) a pulse sequence 26.

Consequently, the switches 11, 16 and 17, if used, will be either (a) closed;
(b) open; or (c) repetitively opening and closing in synchronism with the pulses 26.

FIG. 2 illustrates the type of electronic switches which, preferably, are used as well as the control connections thereto: Opto coupler 11 is formed by a light emitting diode (LED) 30 and a photo resistor 31. Photo resistor 31 is serially connected to the line 10' carrying the tone signals. The capital letters in FIG. 2 correspond to the signals represented by the graphs of FIG. 3.

The opto coupler 11 has a switching control/time characteristic so that, for example, when the switch 24 is changed from reference position R. To supply a positive supply voltage, that is, over to source 25, the brightness emitted by LED 30 rises rapidly, see FIG. 3, graph A, time $t_1$. The resistance value of the photo resistor 31, which receives the light from the LED 30, however, does not drop instantaneously; rather, the resistance value of resistor 31 drops in accordance with an exponential or e-function (see curve 31, graph B of FIG. 3, time interval $t_1 \ldots t_2$). The change in sound level due to the switching ON of the electronic switch 11, that is, the opto coupler, upon suddenly applying the positive voltage from source 25, is illustrated in graph C of FIG. 3, see timing interval $t_1 \ldots t_2$. Graphs A and C of FIG. 3 additionally illustrate the effect upon adding an additional timing circuit 21 with a time constant $\tau_1$. The rapid rise in brightness and loudness level can be delayed or damped. Graph A of FIG. 3 shows, in dotted line, the delay in rise of brightness of the LED 30 and, in dotted line of graph C, the consequent delay in loudness level which, then, will extend the rise time from $t_1$ to $t_2'$. The timing circuit 21 is not strictly necessary if an opto coupler with a suitable time constant is available. In general, the electronic switch 11, that is, the opto coupler, must meet the condition that a tone suppression of at least 60 db occurs if the photo resistor 31 is dark or in its high resistance condition due to entire extinction of the LED 30.

Upon disconnection of the positive voltage from source 25, for example by change-over of switch 24 from the broken line to the solid condition, the brightness of LED 30 drops abruptly—see solid line 30, graph A of FIG. 3. The resistance of the resistor 31 rises gradually in accordance with an e-function, see timing interval $t_3 \ldots t_4$, graph B of FIG. 3. Similarly, the decrease in loudness also is gradual, compare time beyond $t_3$, graph C of FIG. 3. A desired time-level curve is shown in graph D of FIG. 3, which illustrates, click-free or thump-free switching of the tone frequency signal, in which rise and decay of loudness level occurs between predetermined time intervals $T_{ON}$ and $T_{OFF}$.

The second electronic switch 16 is used in conjunction with the first electronic switch 11. Switch 16 and switch 11 both receive the same control voltage from control switch 24. While switch 16 can be an opto coupler with inherent time delay, it is preferred to use an additional timing circuit 22 which, as seen in FIG. 2, utilizes an R/C timing element 32, 33, bridged by a diode 35, and a transistor 34. The second electronic switch 16 likewise is an opto coupler having an LED 36 and a photo resistor 37. The LED 36 is connected in the collector-emitter circuit of transistor 34. The photo resistor 37 is connected in series with the capacitor 38 and, in turn, in a feedback or parallel path of a transistor 39 which forms part of the audio frequency amplifier 12 (FIG. 1). The transistor 34 in the timing circuit 22 acts as an inverter, so that the LED 36 operates in push-pull with respect to the LED 30 of the switch 11, that is, when LED 30 is bright, LED 36 is extinguished, and vice versa. This is also seen in FIG. 3, graph A, in which the broken line curve illustrates the brightness of LED 36, as indicated by the reference numeral 36 in FIG. 3.

OPERATION

Upon change-over of switch 24 from the solid-line to the broken-line position, that is, to positive source 25, resistor 32 of the R/C timing network 32, 33 is bridged by the diode 35. Thus, transistor 34 is changed to blocking condition, with slight time delay. Upon switching back of switch 24 to solid-line position, that is, to reference voltage R, the resistor 32 of the R/C network 32, 33 is fully effective, inhibiting discharge of the capacitor 33 through the diode 35 and only through the resistor 32, so that the brightness of LED 36 rises only slowly—see graph A of FIG. 3, timing interval $t_3 \ldots t_4$, chain-dotted line curve.

The effect of the opto coupler in the feedback or cross-connecting path of the transistor 39 on loudness level is illustrated in FIG. 3, graph C, curve 16, shown in broken line; by adding the timing circuit 22, a time delay will be introduced, shown by curve 16+22, chain-dotted curve, graph C of FIG. 3. Neither of the curves 16—broken line, nor 16+22—chain-dotted line, conform to the requirements of turn-off. The combination of switching time effects due to the electronic switch 11 and 16, jointly, however, and the effects of the two opto coupler provide the appropriate level—time relationship illustrated in graph D of FIG. 3.

The third electronic switch 17 and the associated timing circuit 23 are preferably also used. The timing circuit 23 has an R/C element 40, 41, formed by a capacitor 41 connected between a base of a transistor 42 and ground, and a resistor 40 connected with one end to line 20 and with its other end to the base of transistor 42. The collector of transistor 42 is connected to base of transistor 39 through a capacitor 43. Upon change-over of the switch 24 (FIG. 1) from solid to broken-line position, transistor 42 is controlled to saturation, causing blocking of the transistor 39 with a predetermined and short time delay caused by R/C network 40, 41. This causes a total damping of the audio frequency signal which is higher than the damping caused by the switches 11, 16, respectively. Upon change-over of switch 24, thus, to ground potential, that is, upon turn-OFF of the audio signal, the timing effect of the R/C network 40, 41 of timing circuit 17 becomes effective. Consequently, transistor 39 is controlled to saturation only with some time delay. By introducing the third electronic switch 17, and the timing circuit 23, the match of the turn-OFF characteristics, as well as the turn-ON characteristics of the overall circuit to the desired curve of graph D of FIG. 3 is improved.

Figure 4:
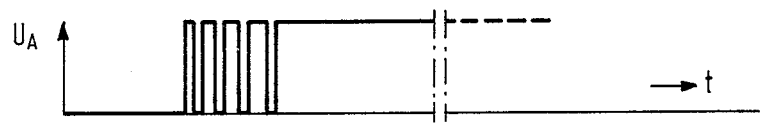
FIG. 4 is a timing diagram of a pulse width modulated control voltage.

It has been found desirable to utilize field effect transistors (FETs) for the transistors in the switches; this is particularly desirable for the third transistor 42, which is directly controlled from the control line 20, and hence from source 25, see FIG. 2a in which FET 42' replaces transistor 42. It is also desirable to control at least one of the electronic switches, for example switch 16, or its LED 36, respectively, by a pulse width modulated control voltage derived from a pulse generator, the average value of which changes, for example increases—see FIG. 4. The switching sequence must be above supersonic level.

In an operating example, the following time periods are suitable:

|  | range | preferred |
|---|---|---|
| $t_1-t_2$ | 1 ... 5 ms | 5 ms |
| $t_1-t_2'$ | ... 100 ms | 80 ms |
| $t_3-t_4$ | ... 100 ms | 80 ms |
| $t_{ON}, t_{OFF}$ | 5 ... 100 ms (ANSI) | 80 ms |

These time periods can easily be realized by use of timing circuit

32/33 of: time constant $\tau_1 = R \cdot C \approx 50$ ms

40/41 of: time constant $\tau_2 = R \cdot C > \tau_1$ the foregoing suitable for a supply voltage $U_b$ (FIG. 2) supplied by source 25 of 9 V.

The dotted line in graph C beyond time $t_3$ shows the composite of loudness level obtained by the combination of the switching characteristics of switches 11 and 16, together with the timing element 22, or a similar switching time characteristic in a suitable opto coupler.

Suitable opto couplers for elements 11, 16, 17 are: photo resistor 31, 37: Clairex CL 703, LED 30, 36: OSHINO D 302.

The dotted lines in graph A of FIG. 3 are shown for reference purposes and correspond roughly to the desired overall tone level also shown in graph D of FIG. 3.

The slow resistance recovery of the resistor 31 of opto coupler 11 (FIG. 2) would extend the turn-off time $t_3 \ldots t_4$ (graph B, FIG. 3) for too long a period and, therefore, the time is cut off by the delayed response of the opto coupler 16, see graph C, chain-dotted line 16+22, so that the composite turn-off time will be shown by the dotted curve beyond time $t_3$. The switch 17 further modifies the characteristic to obtain that shown in graph D of FIG. 3.

I claim:

1. Soft-switching audiometer having
   a source (10) of audio signals;
   an amplifier (12) connected to the source, and an audio transducer (13) providing amplified audio output;
   a first switch (11) serially connected between the source (10) and the amplifier;
   and a switch control unit (24; 25, 26, R) to control switch operation,
   and wherein, in accordance with the invention,
   a second switch (16) is connected in a circuit path across the input-output terminals (14, 15) of the amplifier;
   said first switch (11) and said second switch (16) are electronic controlled switches, both being connected to and controlled to open and close by the switch control unit;
   and both said first and second switches have a current passing/current blocking vs. time characteristic which results in a current rise, or decay, respectively, which is close to but different from abrupt change in current level yet providing rapid level and, below the rate of level change resulting in perceived switching clicks upon connection and disconnection of a circuit path from said audio source (10) through the amplifier (12) to the transducer (13).

2. Audiometer according to claim 1, further including a third electronic controlled switch (17) connected to the input of the amplifier to, selectively, ground the input of the amplifier, as controlled by said switch control unit.

3. Audiometer according to claim 1 or 2, wherein said switch control unit controls operation of said electronic switches in synchronism.

4. Audiometer according to claim 1 or 2, wherein at least one of the electronic switches comprises an opto coupler.

5. Audiometer according to claim 1, wherein at least one of the electronic switches includes a field effect transistor (FET).

6. Audiometer according to claim 1, wherein said switch control unit includes a pulse source (26) providing a pulse width modulated control voltage having an average value of increasing or decreasing level, and a pulse repetition frequency which is above audible range.

7. Audiometer according to claim 1 or 2, wherein the electronic controlled switches include a timing circuit (21, 22, 23) and a switching element, the timing circuit being connected between the switch control unit and the respectively controlled switching element to control the response time characteristic of the respective switch.

8. Audiometer according to claim 1 or 2, wherein the electronic controlled switches include a timing circuit (22) and a switching element, the timing circuit being serially connected between the control unit and the respective switching element and introducing a response delay of the respective switch with respect to a control signal from the switching control unit.

9. Audiometer according to claim 7, wherein the timing circuit includes an R/C element (32, 33; 40, 41).

10. Audiometer according to claim 9, further including means (35) for sensing whether the switching element is to be turned ON or OFF to form two operating modes, and for changing the time constant of the timing circuit in accordance with a selected operating mode.

11. Audiometer according to claim 10, wherein said mode sensing element comprises a diode bridging the resistance component (32) of the R/C element.

12. Audiometer according to claim 1 wherein the first and second controlled switches change the current level gradually during up to 100 milliseconds (ms) but in not less than 5 ms.

13. Audiometer according to claim 1 wherein the first and second controlled switches change the current level gradually during up to 80 milliseconds (ms) but in not less than 5 ms.

14. Audiometer according to claim 1 wherein the first and second controlled switches change the current level gradually during up to 50 milliseconds (ms) but in not less than 5 ms.

* * * * *